US00PP14193P29

(12) United States Plant Patent
Otani

(10) Patent No.: US PP14,193 P2
(45) Date of Patent: Sep. 30, 2003

(54) GRAPE NAMED 'SARAH ANNE'

(50) Latin Name: *Vitis vinifera*
Varietal Denomination: Sarah Anne

(75) Inventor: Hideki Otani, 1960 13th St., Reedley, CA (US) 93754

(73) Assignees: Richard A. Schellenberg, Reedley, CA (US); Hideki Otani, Reedley, CA (US); part interest ( * ) Notice: Subject to any disclaimer, the term of this patent is extended or adjusted under 35 U.S.C. 154(b) by 16 days.

(21) Appl. No.: 09/650,900

(22) Filed: Aug. 30, 2000

(51) Int. Cl.[7] ..... A01H 5/00
(52) U.S. Cl. ..... Plt./205
(58) Field of Search ..... Plt./205

(56) References Cited

U.S. PATENT DOCUMENTS

| | | | |
|---|---|---|---|
| PP5,856 | P | 1/1987 | Garabedian |
| PP6,295 | P | 9/1988 | Tzori |
| PP7,377 | P | 11/1990 | Antcliff |
| PP9,039 | P | 1/1995 | Larson |
| PP9,040 | P | 1/1995 | Larson |
| PP9,224 | P | 8/1995 | Ison |
| PP9,225 | P | 8/1995 | Ison |
| PP9,454 | P | 2/1996 | Mortensen |
| PP9,575 | P | 6/1996 | Ruhl |
| PP9,865 | P | 4/1997 | Ralli et al. |
| PP11,012 | P | 7/1999 | Reisch et al. |
| PP11,260 | P | 3/2000 | Lane |

OTHER PUBLICATIONS

U.S. Trademark Reg. No. 2,364,723, for the mark "PEONY" and indicating a first date of use as Sep. 2, 1999.
California Grape Acreage Report, 1998 Crop (4 pgs.).
Counry of Fresno, California Department of Agriculture Crop Report for the week ending Saturday, Aug. 21, 1999 (2 pgs.).
Webpage from "www.grape.pictures.com" (1 pg.).
Resume of Yuka Watanabe showing research paper on Kyoho (2 pgs.).
Summary of article entitled "Grapevine Virus B Isolated from Grapevines Showing Rugose Wood Symptoms in Japan" (1 pg.).
"Welcome to Nagano" webpage describing Kyoho (2 pgs.).
Resume of Qiang Zhao showing research papers on Kyoho (2 pgs.).
Webpage "Kyoho Grapes" describing Kyoho–harvest in Japan (1 pg.).
Website entitled "Pomology" describing "Kyoho" (2 pgs.).
Summary of article "Effect of GA3 and KT–30 on Fruit Set and Quality in Kyoho Grape" (2 pgs.).

*Primary Examiner*—Bruce R. Campell
*Assistant Examiner*—Michelle Kizilkaya
(74) *Attorney, Agent, or Firm*—Staas & Halsey LLP

(57) ABSTRACT

A new variety of grape is disclosed characterized by darker color, smaller size, more oblong shape and sweeter taste than the 'Kyoho' grape.

13 Drawing Sheets

BACKGROUND OF THE INVENTION

The present invention relates to a new and distinct variety of grape given the denomination 'Sarah Anne'.

The parent variety of grape is commonly known as 'Kyoho', and is a popular unpatented table grape and syrup grape grown predominantly in Japan, but also grown here in the U.S. Most particularly, the 'Kyoho' is grown in Southern California, where it usually ripens in early August.

SUMMARY OF THE INVENTION

This new variety 'Sarah Anne' is characterized by a darker, somewhat smaller, more oblong, and more intense, sweet flavor than the known 'Kyoho' variety.

BRIEF DESCRIPTION OF THE DRAWINGS

Each of the photos described below relates to various stages of development of the new variety, unless otherwise noted. The photos depict 'Sarah Anne' plants of approximately three years of age.

DETAILED BOTANICAL DESCRIPTION

A. Genus and Species: *Vitis vinifera.*

Figure 1:
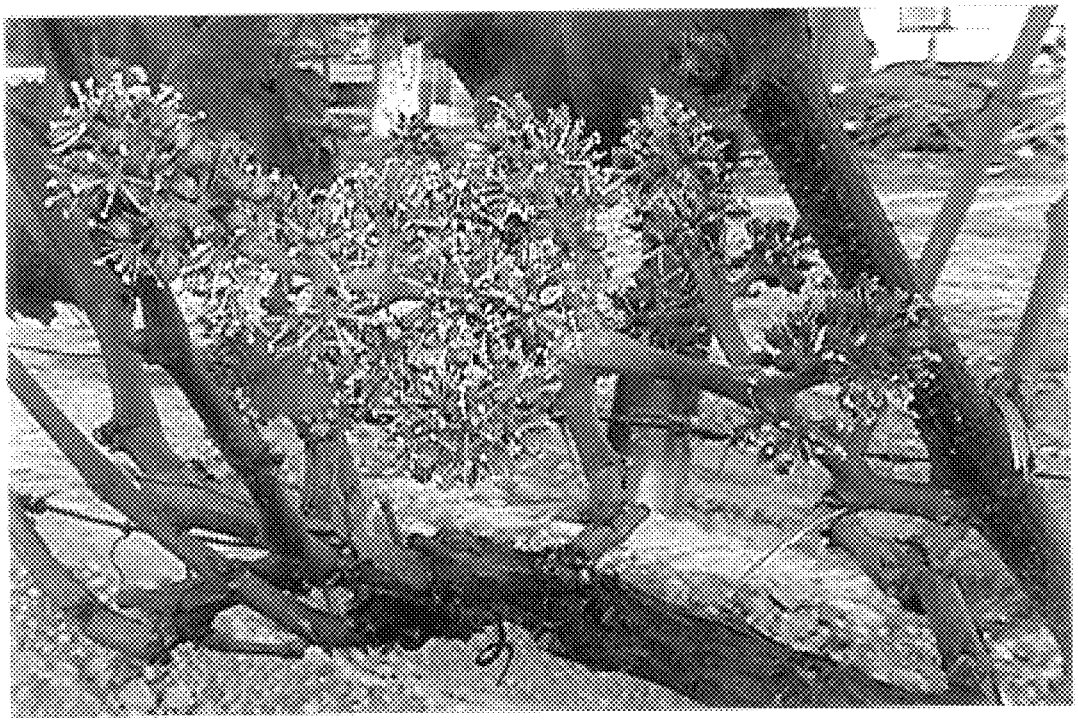
FIG. 1 illustrates a typical flower cluster of the new variety.
Figure 2:
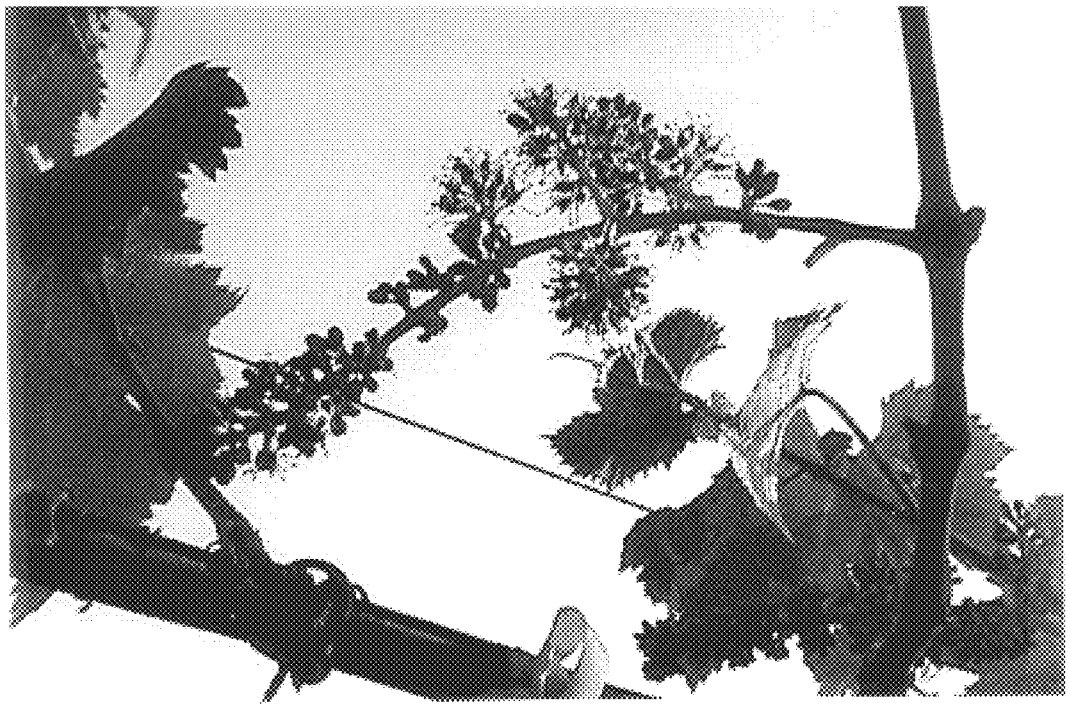
FIG. 2 illustrates another typical flower cluster of the new variety.
Figure 3:
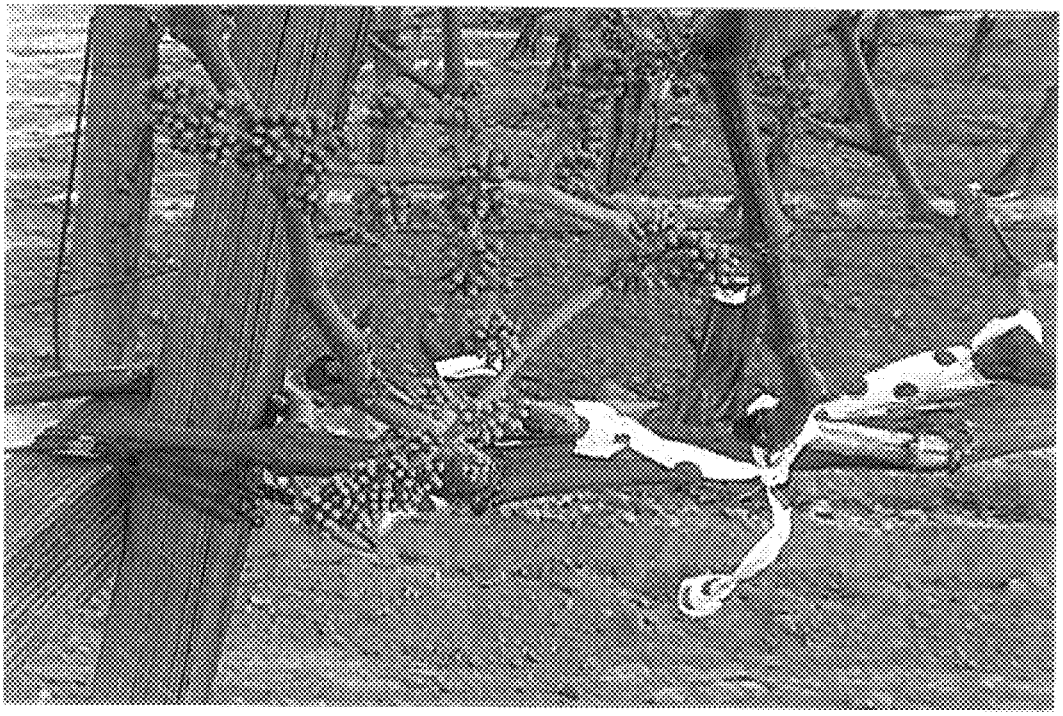
FIG. 3 illustrates early berry formation of the new variety.
Figure 4:
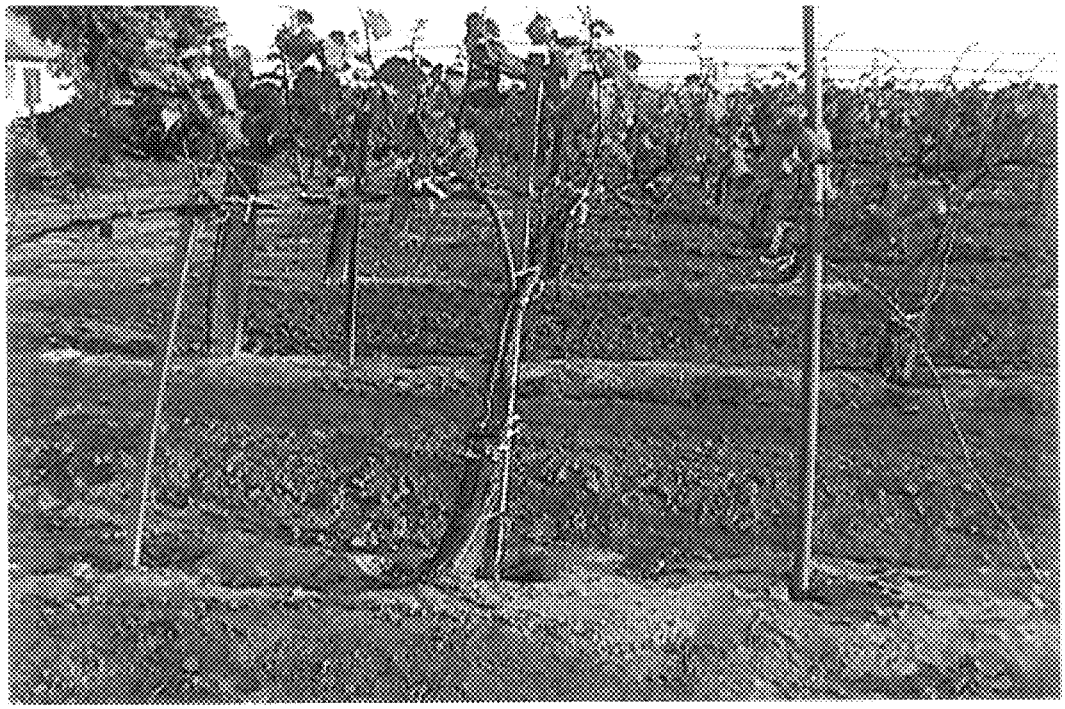
FIG. 4 illustrates typical vines of the new variety.
Figure 5:
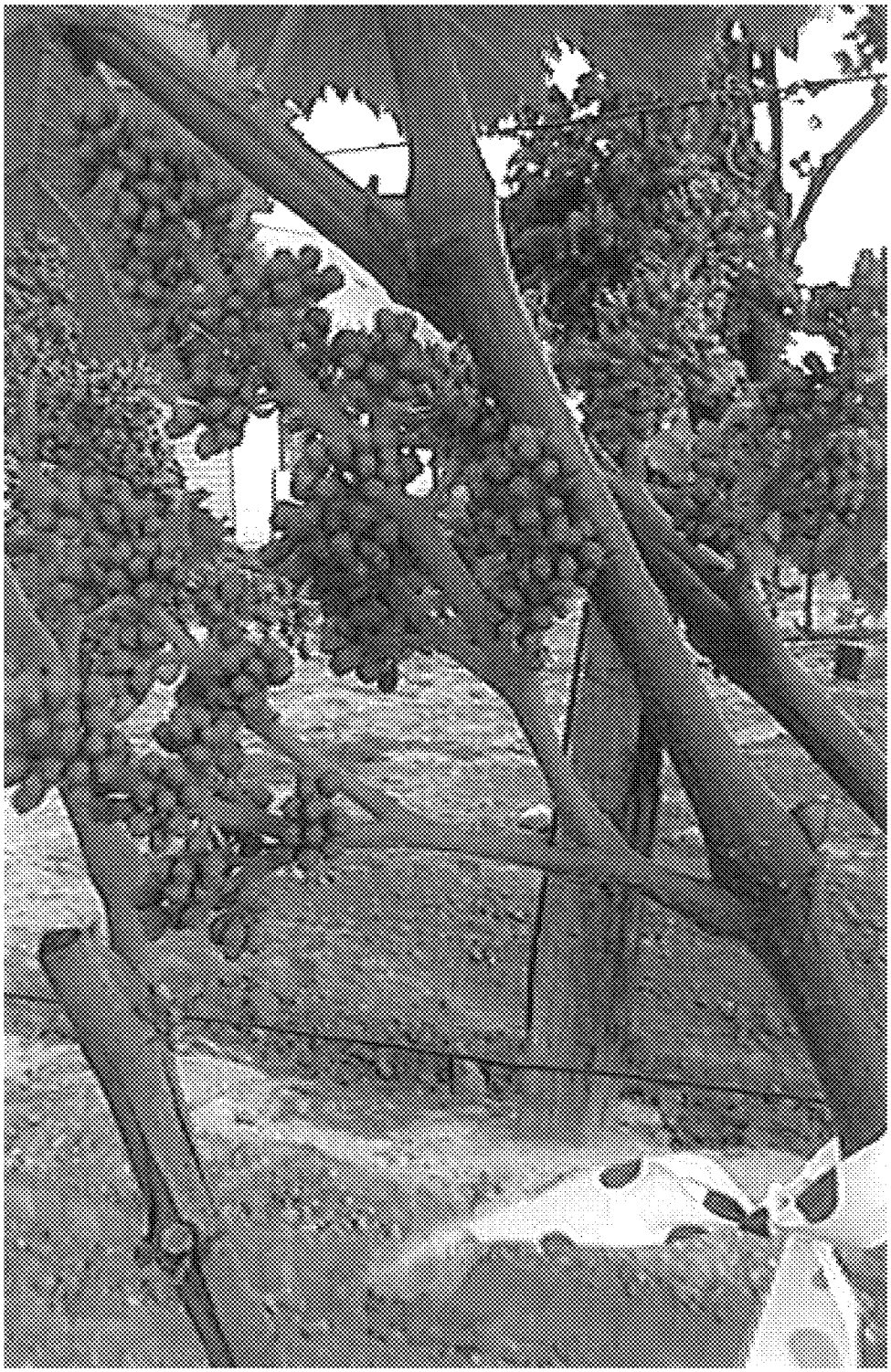
FIG. 5 illustrates further berry formation of the new variety.
Figure 6:
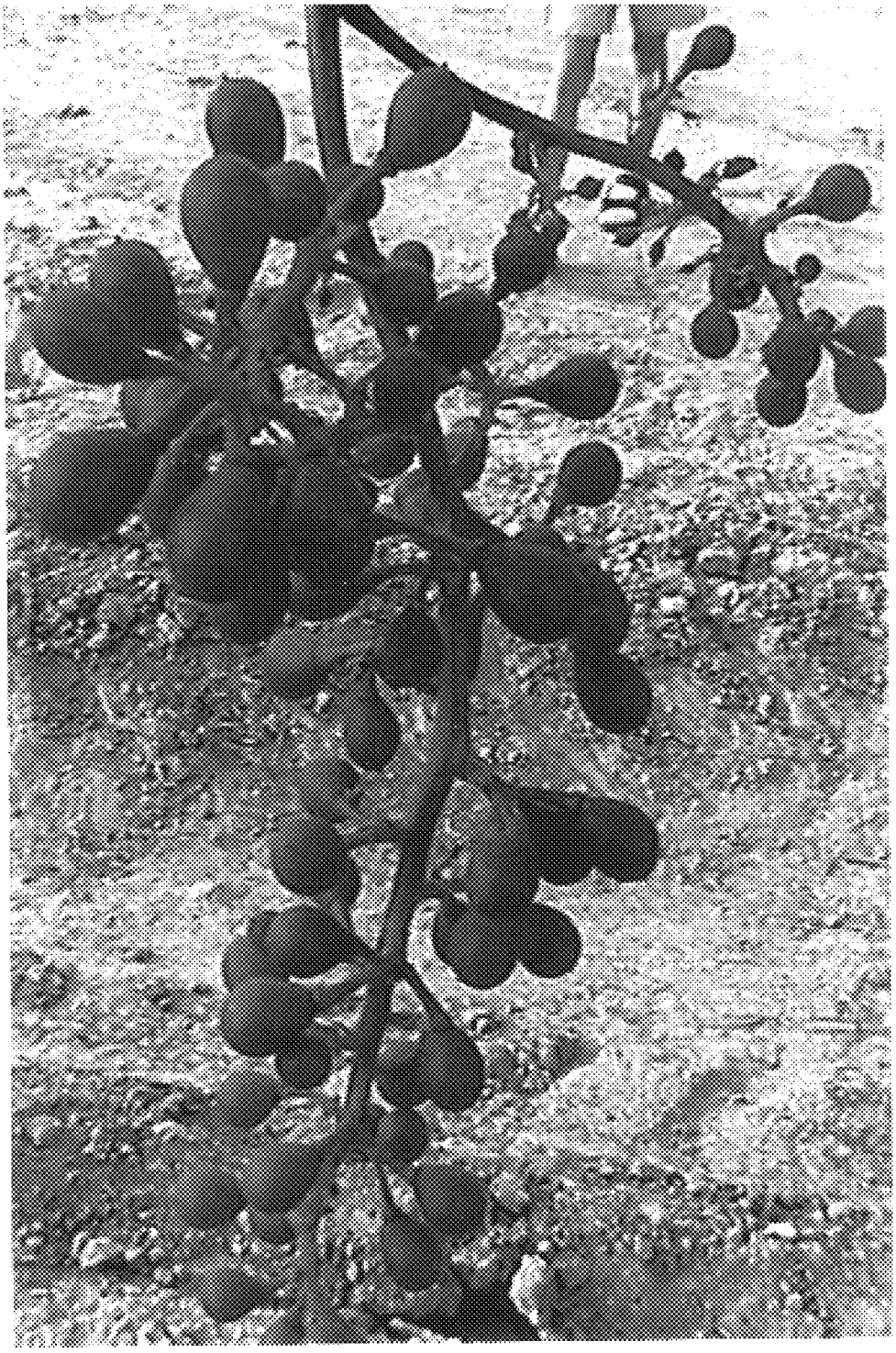
FIG. 6 illustrates still further berry formation of the new variety.
Figure 7:
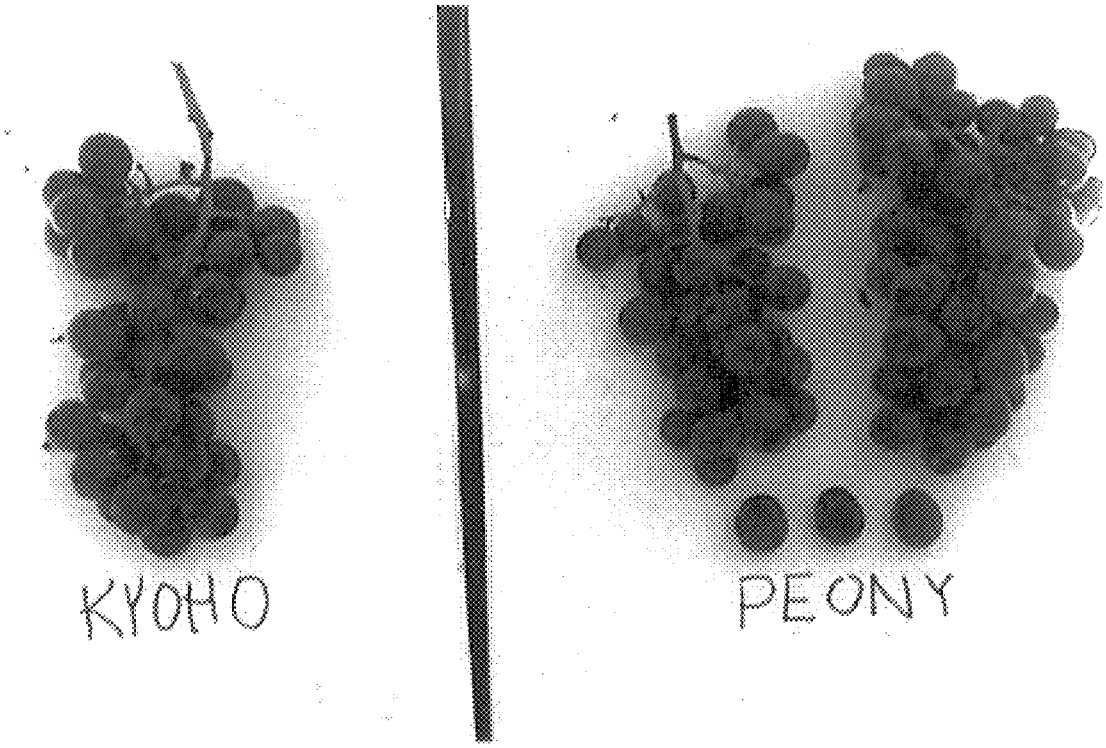
FIG. 7 illustrates a typical cluster of 'Kyoho' grapes versus a cluster of grapes of the new variety 'Sarah Anne'.
Figure 8:
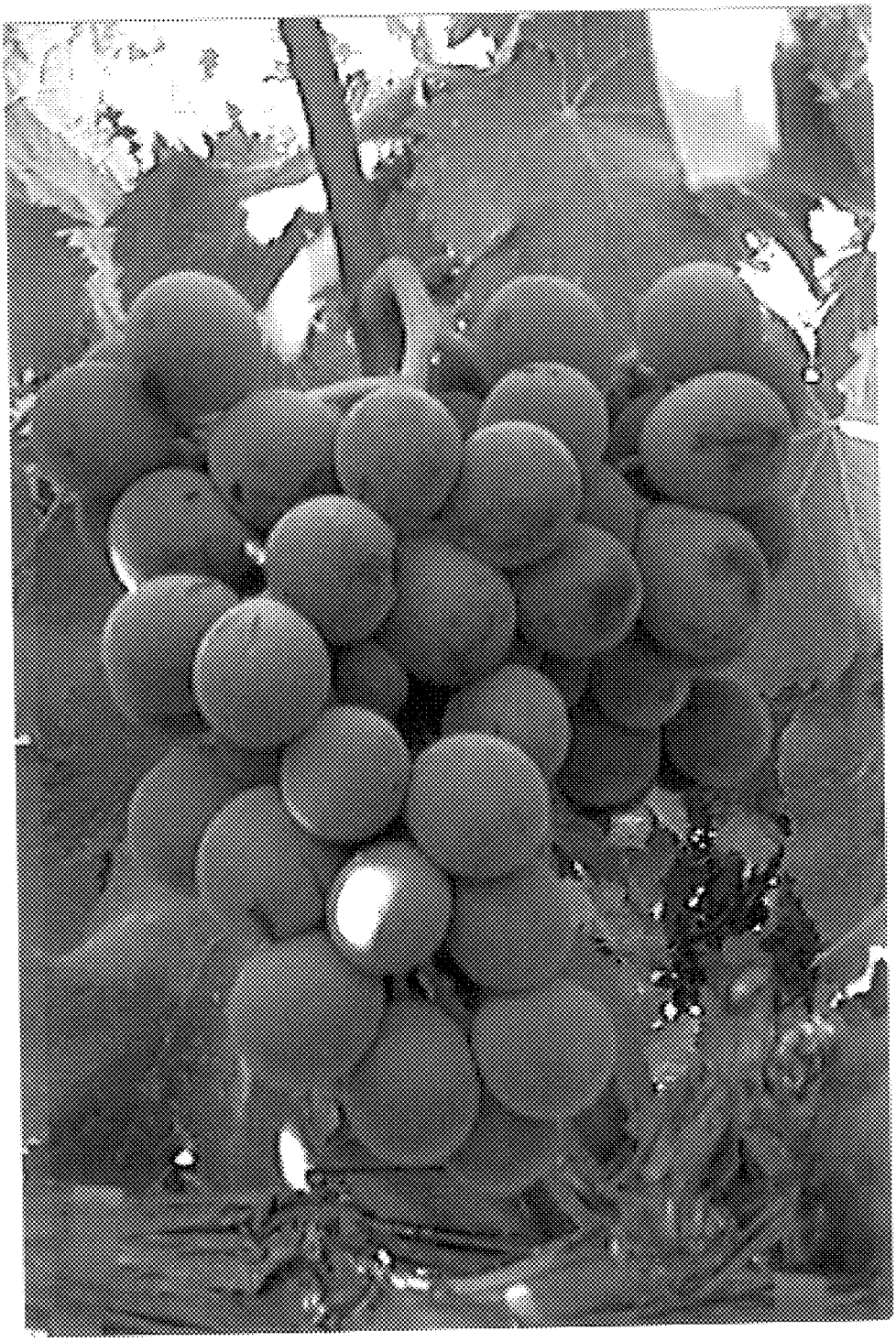
FIG. 8 illustrates a typical cluster of grapes of the new variety 'Sarah Anne' plant.
Figure 9:
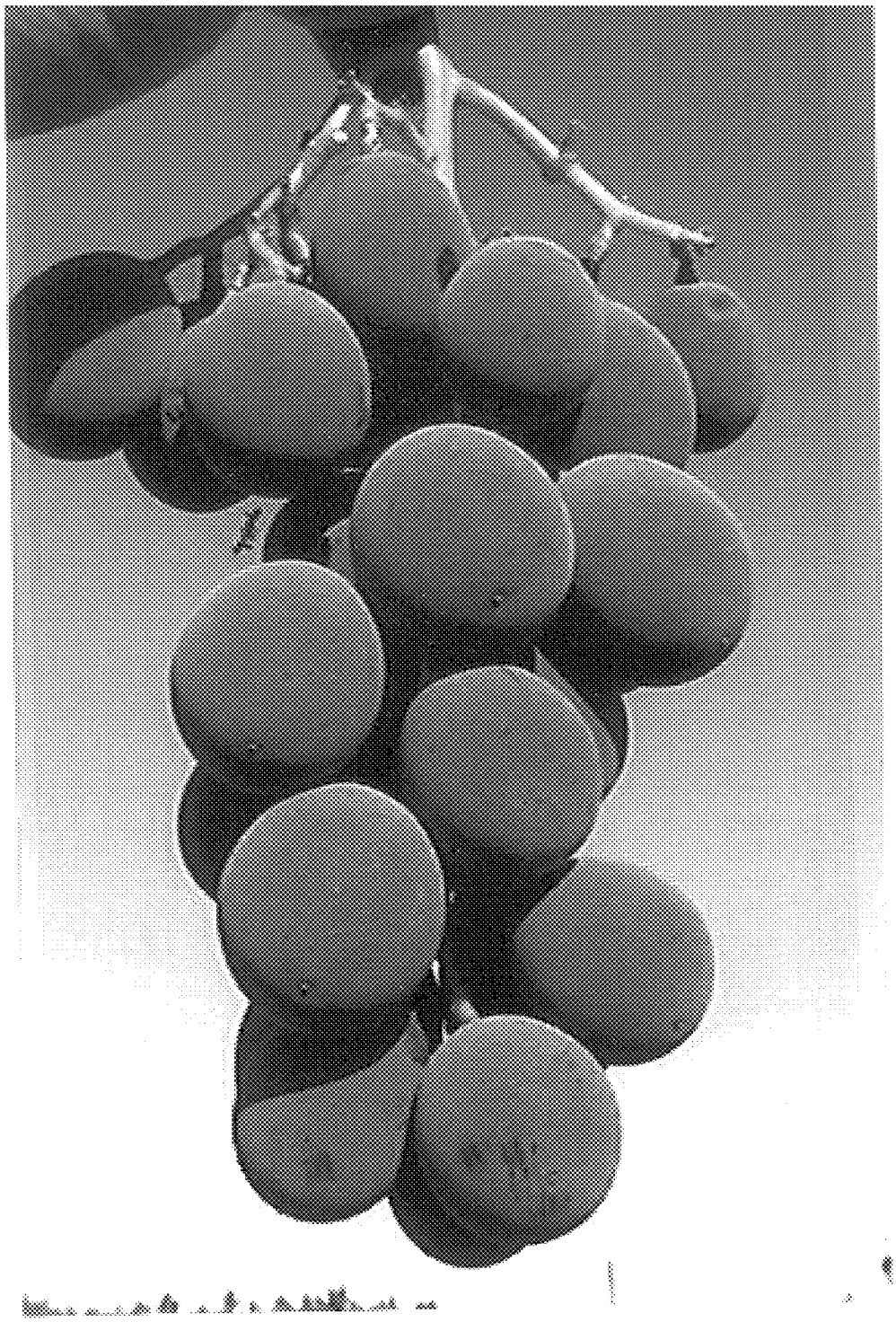
FIG. 9 illustrates a typical cluster of grapes of the new variety 'Sarah Anne' plant.
Figure 10:
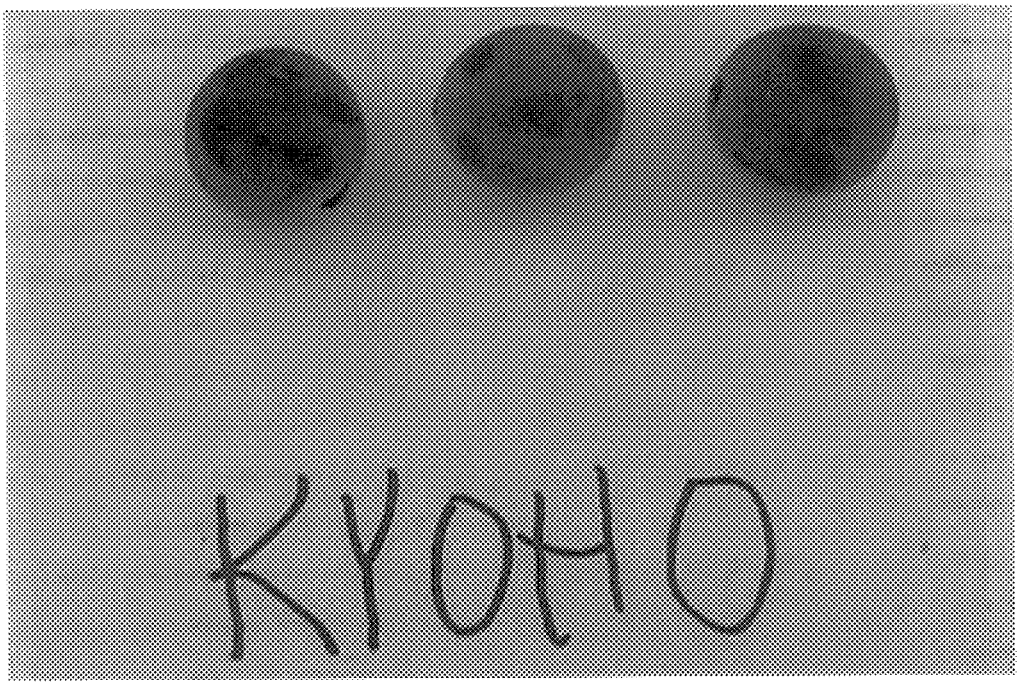
FIG. 10 illustrates individual 'Kyoho' grapes.
Figure 11:
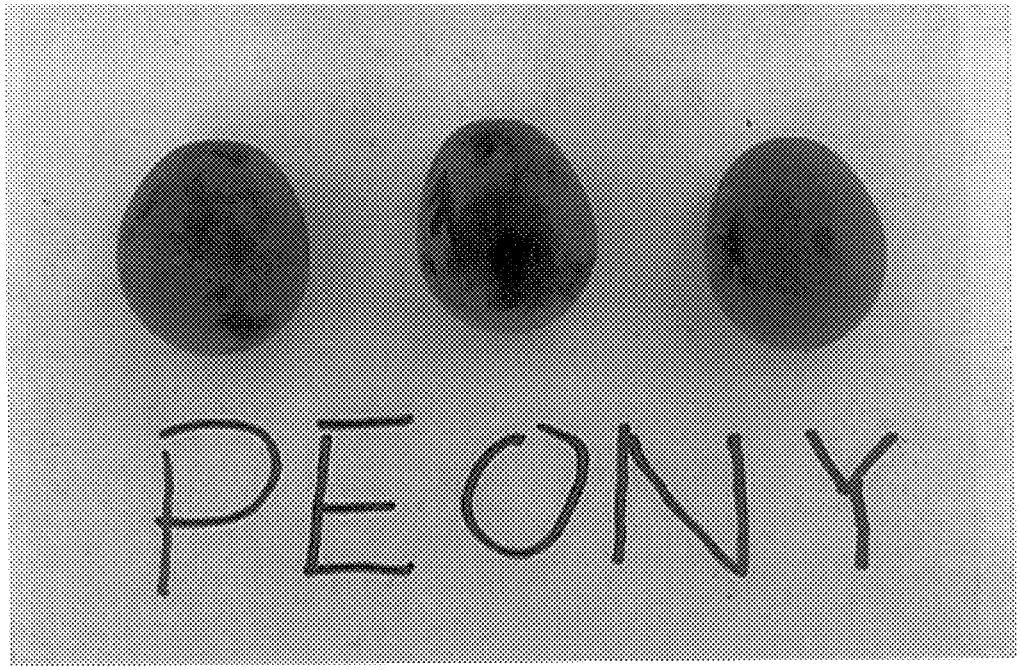
FIG. 11 illustrates individual grapes of the new variety.
Figure 12:
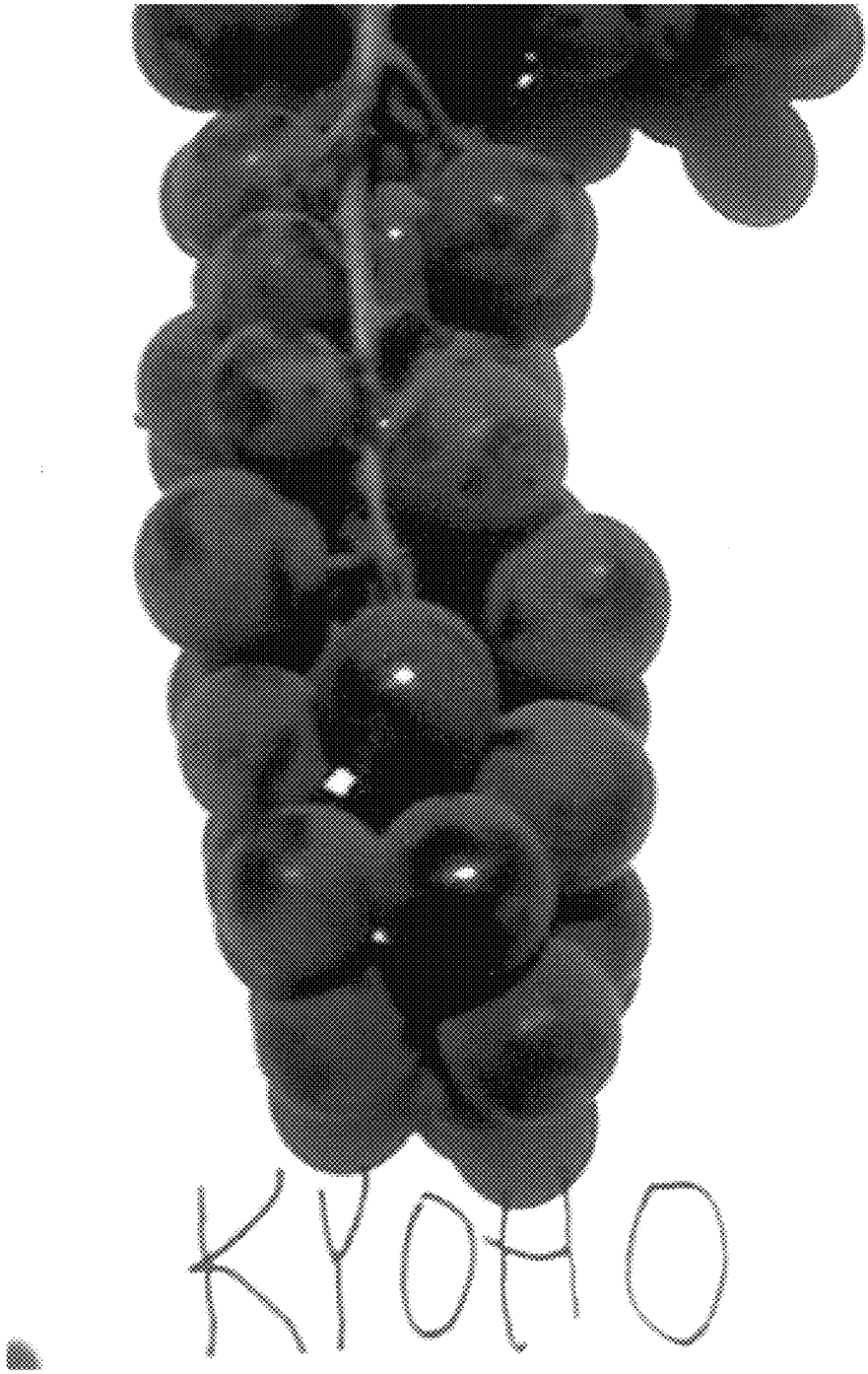
FIG. 12 illustrates a 'Kyoho' grape cluster.
Figure 13:
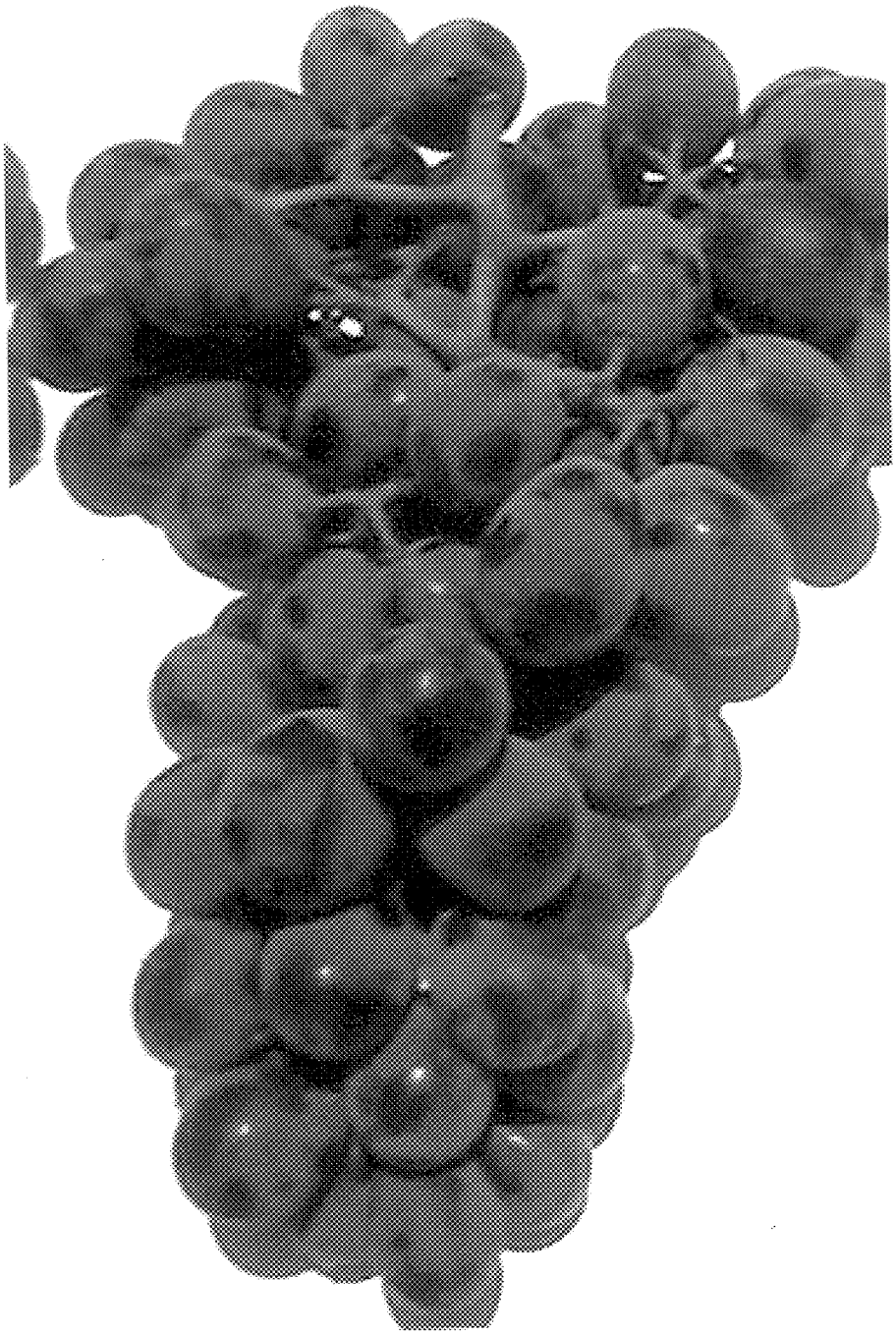
FIG. 13 illustrates a grape cluster of the new variety.
Figure 14:
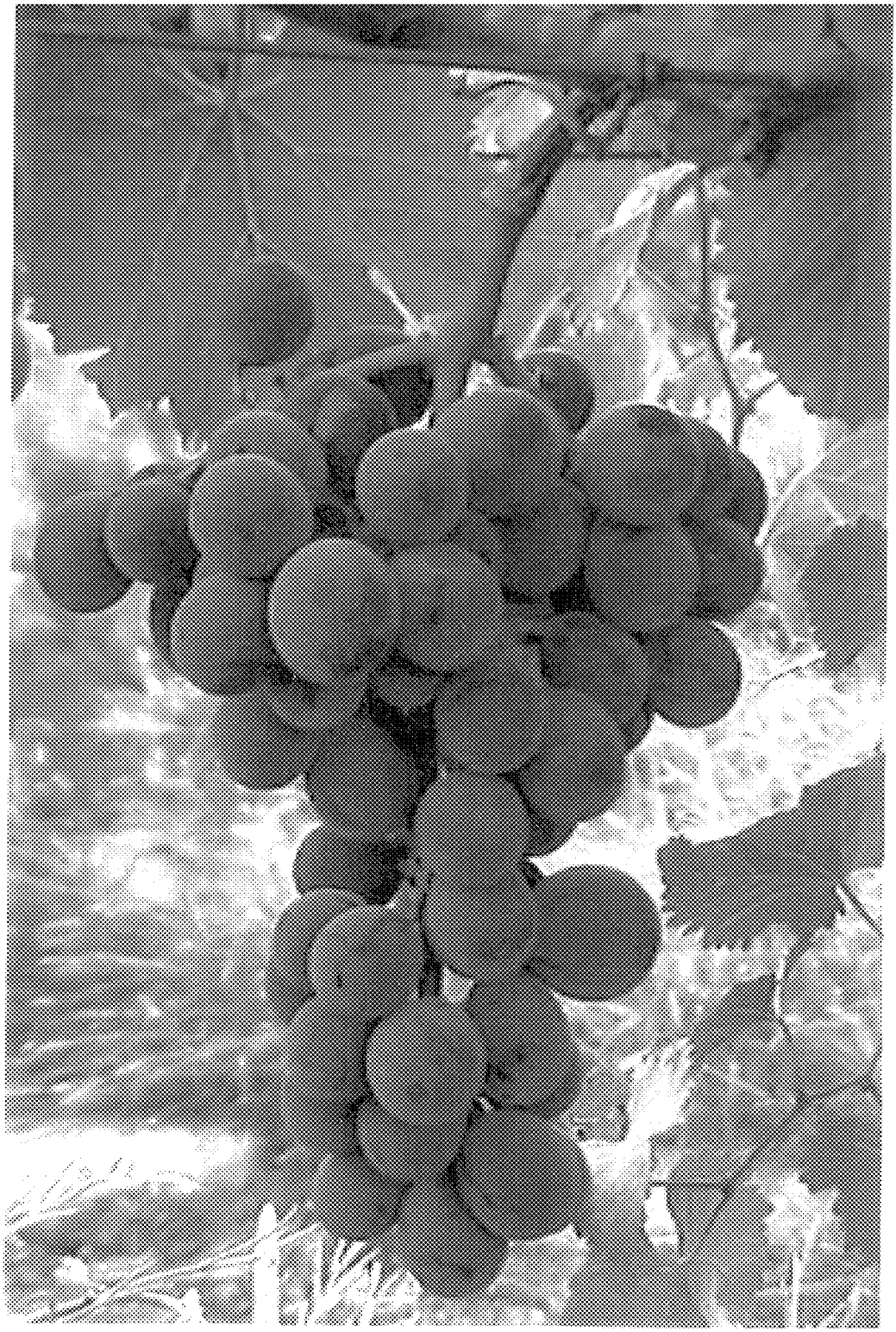
FIG. 14 illustrates a grape cluster of the new variety.
Figure 15:
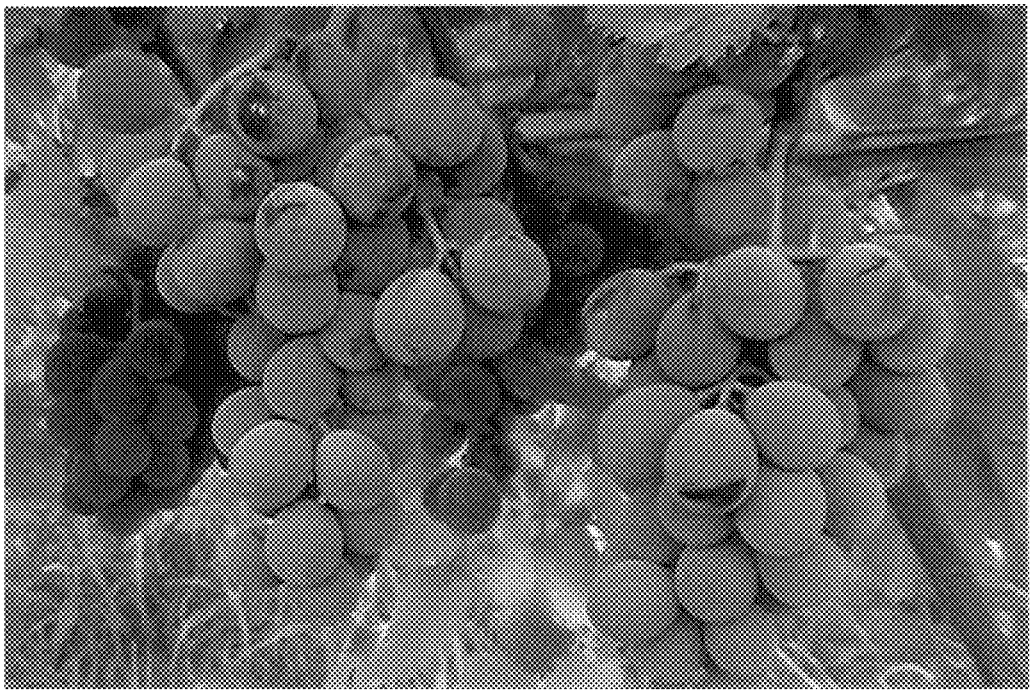
FIG. 15 illustrates a grape cluster of the new variety.
Figure 16:
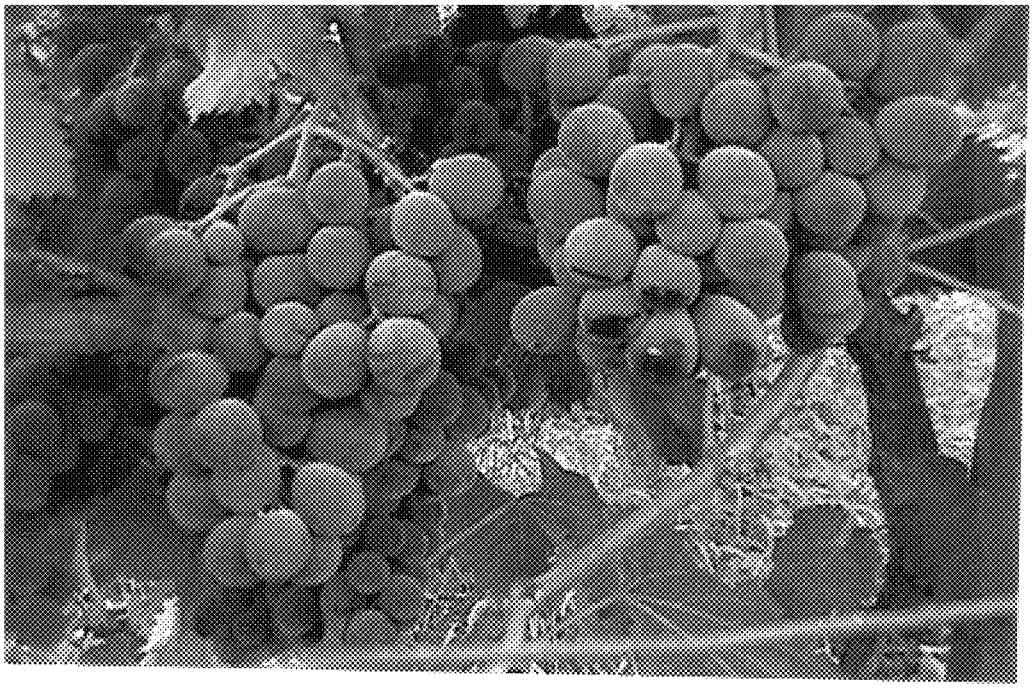
FIG. 16 illustrates a grape cluster of the new variety.
Figure 17:
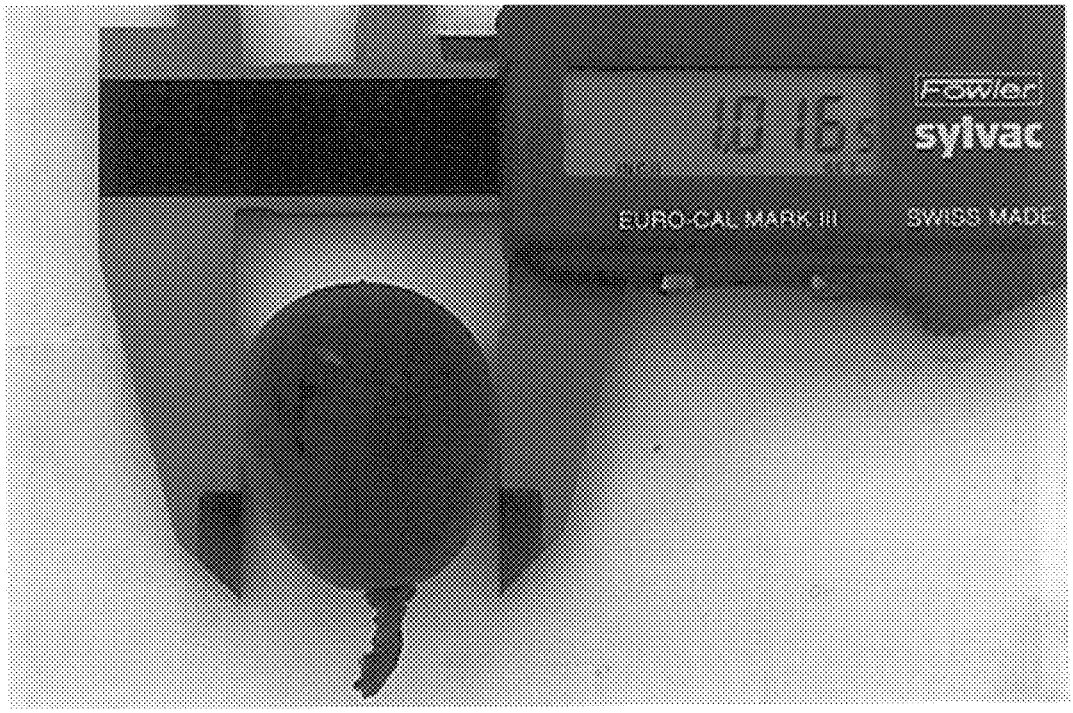
FIG. 17 illustrates measurement of the width of a grape of the new variety.
Figure 18:
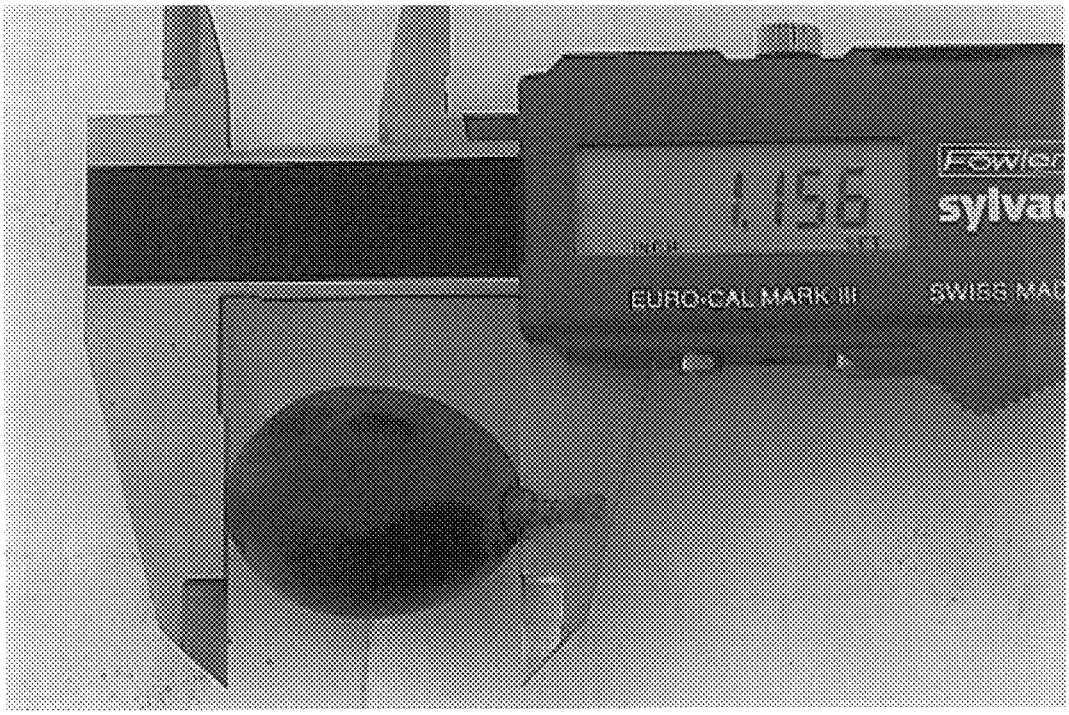
FIG. 18 illustrates measurement of the length of the grape of the new variety.

B. Name: 'Sarah Anne'.

C. Type/Market: Table Grape.

D. Characteristics.

1. Origin of the New Variety

About twenty years ago, some scion wood of a 'Kyoho' grape vine was brought from Japan to the U.S., and was grafted to a 'Thompson Seedless' grape vine in Fresno, Calif. 'Thompson Seedless' is believed to be an unpatented variety. Accordingly, the parent plant from which the new 'Sarah Anne' variety was cultivated was the 'Kyoho' grafted to a 'Thompson Seedless' rootstock. After a few years, there was enough Kyoho scion wood grown from the first grafted plant, described above, to graft several more 'Thompson Seedless' grape vine rootstocks. It is from this second group of vines, when a mutation apparently occurred, and was noticed by the inventor as the unique variety described herein.

Then, about eight years ago, the inventor took scion wood from this mutated group of vines and grafted them to several Emperor rootstocks in Reedley, Calif. Emperor is also believed to be an unpatented variety. Each of this group of grafted vines maintained the same unusual characteristics that existed from the mutated vines. About four years ago, the inventor took scion wood from these vines and grafted them to several hundred more 'Emperor' vines in Reedley, Calif. They continued to maintain the same unique characteristics. All of the available graft wood from the patch of unique plants have been gleaned during the past two years and fifteen acres of 'Emperor' grapes have now been successfully grafted over to the 'Sarah Anne'.

Accordingly, thses grapes have been asexually reproduced true to the type of the original vine in all distinguishing characteristics of darker color, smaller grape, more oblong shape and sweeter taste to establish that these claimed characteristics are stable.

From the plants in Reedley, Calif., about 160, 5-kilo containers of 'Sarah Anne' grapes were packed. Samples thereof were shipped on Sep. 2, 1999 to test reaction and marketability of the new grape.

2. Vine

The growth of the vine is of moderate vigor. It has been experimentally grafted to known rootstocks, including Emperor, and it has been grown on its own natural root. These rootstalk trials all produced vines of similarly moderate vigor. The foliage is somewhat sparse and certainly would not be considered dense.

A commercial 'Sarah Anne' vineyard was planted using '5BB' rootstock, a commercially grown rootstock commonly chosen for its vigorous tendencies and for its ability to survive and even flourish in soils with poor water drainage and permeability problems. This rootstock planting occurred in the Spring of 2000. As soon as the 5BB rootstock buds began to smell, the 'Sarah Anne' buds were grafted thereto. Most of the vines reached a training wire at 42" by mid-July 2000 and were pruned back pending the installation of an open gable trellis system installed in the Winter of 2000. The vines were trained in a quadrilateral cordon design. By August 2002, average trunk size of 1.25" to 1.5" in diameter was seen. The texture of the trunk is quite woody and rough and light redish brown in color. The lateral cordons are approximately 0.75" in diameter and appear to be mature as indicated by the woody and rough appearance. The vertical canes which grew from the quadrilateral cordons in the Spring of 2002 are green and lush and bear much fruit. They have grown an average of 6 feet in length, some a little shorter and some as long as 11 feet. During late August, lignification begins to occur on the yearling shoots extending about to where the grape bunches are attached by the peduncle to the shoot. It is late December before the lignification extends to near the end of the shoot.

The vine is extremely fruitful. It is growing a first crop which will begin to be harvested Aug. 6, 2002. Also growing concurrently is a second crop which will yield a volume of about 20%–40% of the size of the first crop and will ripen toward the end of September, 2002. This second crop is commercially viable in terms of quantity and quality and provides an opportunity for an extended marketing period.

The grapes and stems seem to be quite resistant to mildew. Some of the young vines have not received any fungicide application this year and show no signs of mildew except on the leaves and shoots.

3. Leaves

The leaves of the 'Kyoho' and the 'Sarah Anne' are similar in structure and appearance.

The leaves when mature are medium in size and range from 3" to 6" in diameter and are pentagonal in shape. If one draws a circle around the leaf, one would find that the leaf is about as wide as it is long except for a deeply cut "U"-shaped sinus where the petiole attaches to the leaf. The petiole is light green and is about ⅓ the length of the width of its respective leaf. The veins in the leaf are also green and protrude prominently from the surface of the underside of the leaf, which has a matte dull texture. The face of the leaf is relatively smooth and glossy. The new growth of leaves at the end of the shoot are light green in color and covered face and back with white prostrate hairs, no erect hairs. As the newly formed leaves mature, they lose their prostrate hairs, first on the face of the leaf and finally on the back of the leaf. As the surface of the leaf matures, the face of the leaf becomes somewhat glossy and becomes a darker, deeper green in color.

4. Shoots

As the shoots develop both surfaces of the newly formed leaves at the tip of the shoot are covered with dense prostrate hairs.

Each new leaf has another bud at the base of the petiole where the leaf attaches to the shoot. Almost every new leaf also has a tendril attached to the shoot on the opposing side of the shoot from where the petiole is attached. The phenomenon of tendrils opposing each leaf seems to change as the shoot nears the point of attachment on the cordon from which it is growing. At the tip of the shoot where the new growth occurs the color of the shoot is light green. The shoot becomes slightly darker green as it approaches the main cordon and can have some streaks of red along the way. Almost every tendril has 3 tips and, when mature, is 5"–6" long. As you follow the shoot from the tip to the cordon you will observe the secondary bud at the base of each petiole sprouting a new shoot. These secondary shoots can grow quite long as the main shoot approaches the cordon. The secondary shoot varies in length and may sometimes exceed 2 feet.

5. Flowers

In 2000, the 'Sarah Anne' grape vine's flowers bloom began around the 5th of May, and finished quite evenly about a week later. The flowering nodes are numerous and the pistols are almost white in color and are easily visible against the light green background of the bunch cluster. Bunch clusters are generally 6"–7" in length. The crop was quite heavy. The bunches were thinned to an average of one bunch per chute, sixteen to twenty-six bunches per vine. After the bloom, the grape bunches went through their own natural berry thinning process called "shatter." The shatter that took place this year was extreme. Many branches were left with fewer berries than were needed to develop into well formed, appropriately sized bunches. This excessive shatter may have resulted from experimentation with bunch thinning, tipping and bunch shaping. The 'Sarah Anne' vines of the control group seemed to have a more consistent berry set but still less than desirable.

6. Ripening

Harvesting of the 'Kyoho' occurred in Sanger, Calif.

Grape maturity factors indicate that some of the 'Sarah Anne' could have been harvested at the same time as the 'Kyoho', however, the 'Sarah Anne' seems to hold well on the vine and can be harvested at a later date without compromising quality.

Harvest of a first crop usually begins during the first week of August and concludes during the first week of September. A second crop can usually be harvested beginning the last week in September and conclude during the later weeks of October.

7. Fruit a. Berry

1. Shape: Somewhat oblong, tapering slightly toward the stem of the grape. When the 'Sarah Anne's very round shape is compared to the 'Emperor', the 'Emperor' has sort of a tear-drop shape, rather narrow on the stem end and wider on the bloom end. A nicely shaped 'Thompson Seedless' table grape, on the other hand, is almost cylindrical in shape, with the diameter of the stem end nearly equivalent to the diameter of the bloom end with a slight increased diameter or bulge toward the middle.

2. Size: Grape size may vary considerably from bunch to bunch from about 11/16" to 1⅛" in diameter. The length will vary from 12/16" to greater than 1¼". Compared to the 'Sarah Anne', both the 'Emperor' and 'Thompson' table grapes are generally smaller in diameter and longer.

3. Seeds: Both the berry of the 'Kyoho' and the 'Sarah Anne' contain seeds. The 'Sarah Anne' grape generally contains from 1 to 4 seeds, but most commonly 2–3 seeds per grape. Occasionally one may find a 'Sarah Anne' grape with no seeds. The seeds are about ⅜" long and 3/16" wide, sort of pear shaped and straw colored. From a sample of 50 randomly selected berries there was an average of 2.86 seeds per grape. The average weight of each grape was 9.91 grams. The average weight of each seed was 0.1349 grams. The ratio of grape mass to seed mass is 24.49:1.

4. Color: The color of the mature 'Sarah Anne' grape is much darker purple, almost black, and much sweeter than its parent grape, the red colored Kyoho. Compared to the almost black 'Sarah Anne' seeded table grape, the 'Emperor' is a red seeded table grape and the 'Thompson Seedless' is a white seedless table grape.

5. Skin: The skin of the 'Sarah Anne' is of medium thickness and is covered with a dull waxy bloom. This waxy bloom helps to protect the berry from disease and rain damage. The 'Sarah Anne' grape skin is easy to peel from the light green translucent flesh of the grape. This is an attractive characteristic as some consumers customarily peel their grapes before serving. The skin shows no signs of tendency to split or crack. The skin of the 'Sarah Anne' is what is commonly called a slip skin. It is a soft berry that is easily peeled as is the custom among some ethnic communities. The 'Emperor' and 'Thompson Seedless' are more of a crisp type of berry that will burst in your mouth upon biting down and do not easily peel. The 'Sarah Anne' berry will softly yield to the pressure of biting down and be gently crushed.

6. Bunch Size: The 'Sarah Anne' generally produces bunches of a medium size. A common bunch would consist of between 60–90 berries.

7. Taste: The taste of the 'Sarah Anne' grape is very fruity and very sweet, almost to the point of being syrupy sweet. It has a very fruity aroma that people find pleasant. But, the sweet-fruity aroma also tends to attract birds that can inflict significant damage to the grape crop prior to harvest. Harvesting the 'Sarah Anne' takes place when the brix level of the grape exceeds 20. Both 'Thompson Seedless' grapes and 'Emperor' grapes are harvested around the 17 brix level which yields a moderately sweet grape with no distinctive flavor.

The 'Sarah Anne' grape is very juicy and somewhat soft. When held between one's fingers the grape will readily yield to pressure unlike the crispness of a 'Flame Seedless' or 'Thompson Seedless' grape. The texture of the flesh is soft.

8. Culturing: Cultural practices performed for both the 'Kyoho' and 'Sarah Anne' varieties are similar. They are both spur pruned with a similar number of spurs branching off of two opposing cordons.

The 'Sarah Anne' vines are grown utilizing a quadrilateral cordon on an open gable trellis design. This design successfully opens up the vine and allows for sun light penetration and good air circulation. The vines are spur pruned during the dormant season and copper is applied to the end of each spur to prevent fungi infection.

Prior to bloom the vines are crown suckered. A couple of weeks later leaves are pulled and small clusters are removed to allow for no more than 2 bunches per shoot or 16 to 26 bunches per vine, depending upon the health and vigor of the vine. After the bloom the clusters of grape go through a shatter. In some instances the shatter is excessive not leaving enough berries in the cluster to form a well formed cluster or bunch. In any case no bunch clipping or removal of berries is necessary to allow for proper sizing of berries.

Petiole analyses are performed by a lab at harvest time to determine plant nutrient needs and hence the appropriate supplements are applied.

9. Growth/Vigor: Neither the 'Sarah Anne' nor the 'Kyoho' is a very vigorous growing vine as compared to many other table grapes. Their vigor is comparably similar. They both seem to have cropping tendencies as they are very fruitful and produce many medium sized bunches.

10. Storage: The 'Sarah Anne' grape seems to store quite well. A few boxes were stored through last winter and brought out of cold storage in late April of 2000. Even though a portion of the grapes in the containers was infested by fungi and rot, there was a surprising amount of grapes remaining which were solid, clean and perfectly fit for human consumption.

11. Distinctive Characteristics: The 'Sarah Anne' characteristics were compared with the 'Kyoho' grapes harvested Aug. 5, 2000 in Sanger, Calif.

The grapes of the 'Kyoho' are generally lighter in color, more of a deep red than the almost jet black color of the 'Sarah Anne' grapes of comparable maturity.

On average, the grape size of the 'Kyoho' was slightly larger than the average size of the 'Sarah Anne'.

The shape of the 'Kyoho' grape is very round in comparison to the 'Sarah Anne' which is a bit oblong, tapering toward the stem of the grape.

The most significant difference was in the taste. Both are good tasting. The 'Kyoho' has a similar flavor, but is quite muted in relation to the 'Sarah Anne'. The 'Sarah Anne' flavor is much more intense, full and robust: it is so sweet that it is almost syrupy.

The average Brix (according to the Brix Scale) of a sample of five separate branches of the 'Kyoho' ranged from a low of 15° to a high of 21°. The average Brix of a sample of five bunches of the 'Sarah Anne' picked Aug. 6, 2000 ranged from 23° to 27°. This is a considerable distinction and, at 5° to 8° higher than its parent the Kyoho grape at the same harvest date, was very noticeable upon taste testing.

What is claimed:

1. A new and distinct variety of grape plant, substanitally as described and illustrated.

* * * * *

-FIG. 7